United States Patent [19]

Falk

[11] 4,239,915
[45] Dec. 16, 1980

[54] PERFLUOROALKYL CARBOXYLIC ACIDS

[75] Inventor: Robert A. Falk, New City, N.Y.

[73] Assignee: Ciba-Geigy Corporation, Ardsley, N.Y.

[21] Appl. No.: 747,114

[22] Filed: Dec. 2, 1976

[51] Int. Cl.$^3$ .......................................... C07C 51/347
[52] U.S. Cl. .................................. 562/481; 260/546; 562/426; 562/429; 562/430; 562/556
[58] Field of Search .................. 260/535 H; 562/481, 562/426, 429, 430, 556

[56] References Cited

U.S. PATENT DOCUMENTS

| | | | |
|---|---|---|---|
| 3,544,594 | 12/1970 | Grimm | 560/154 |
| 3,828,098 | 8/1974 | Gilleo | 260/535 H |
| 4,054,596 | 10/1977 | Koshar | 560/150 |

Primary Examiner—Paul J. Killos

Attorney, Agent, or Firm—Michael W. Glynn

[57] ABSTRACT

Gem-perfluoroalkylthio group containing acids of the formula

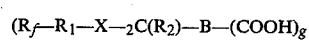

and alkyl esters thereof, wherein $R_f$ is a perfluoroalkyl, $R_1$ is alkylene or alkylenethio- or oxy- or imino- alkylene, $R_2$ is hydrogen, alkyl or phenyl, B is a covalent bond, alkylene or alkanetriyl and g is 1 or 2, can be prepared by the addition of a perfluoroalkylthiol to aldehydo or keto acids or esters. The compounds are useful as surface active agents, as intermediates to fluorochemical chromium complexes with low surface energies, or as oil and water repellents for textiles.

11 Claims, No Drawings

PERFLUOROALKYL CARBOXYLIC ACIDS

DETAILED DISCLOSURE

This invention is directed to perfluoroalkyl group containing acids and esters. Additionally, anhydrides of these acids are obtainable. These compounds are useful in themselves for textile treating or as chromium complexes which possess oil and water repellent properties. They are additionally useful in preparing surface active agents.

The perfluoroalkyl acids have the general structure $$(R_f-R_1-X)_2C(R_2)-B-(COOH)_g$$

wherein $R_f$ is straight or branched chain perfluoroalkyl of 1 to 18 carbon atoms or said perfluoroalkyl substituted by perfluoroalkoxy of 2 to 6 carbon atoms;

$R_1$ is branched or straight chain alkylene of 1 to 12 carbon atoms, alkylenethioalkylene of 2 to 12 carbon atoms, alkyleneoxyalkylene of 2 to 12 carbon atoms or alkyleneiminoalkylene of 2 to 12 carbon atoms where the nitrogen atom contains as a third substituent, hydrogen or alkyl of 1 to 6 carbon atoms;

$R_2$ is hydrogen, straight or branched alkyl, of 1 to 6 carbons, phenyl, alkyl substituted phenyl with up to 18 carbons, or —B—COOH;

B is a covalent bond, alkylene with up to 18 carbon atoms or alkanetriyl with up to 18 carbons g is 1 or 2 with the proviso that if g is 2, $R_2$ is not —B—COOH; if B is a covalent bond or a diradical linkage group, then g is 1 and if B is a triradical linkage group then g is 2. Preferably B is selected from a covalent bond, $$-(CH_2)_{1,2 \text{ or } 3} \text{ and } -C\begin{matrix} H \\ \diagdown \end{matrix}\begin{matrix} (CH_2)_2- \\ (CH_2)_2- \end{matrix}$$

and X is —S—, —SO—, or —SO$_2$—.

The novel $R_f$-acids containing sulfide linkage are obtained by the acid catalyzed addition of $R_f$-thiols to aldehydo or keto acids of formula $$O=C(R')-B-(COOH)_g$$

$R_f$-acids containing sulfoxide or sulfone linkages are obtained by oxidizing $R_f$-acids with sulfide linkages to the desired oxidation state as described in Reid, Organic Chemistry of Bivalent Sulfur, Volume III, page 333 (Chemical Publishing Co., Inc., New York).

Perfluoroalkyl thiols useful herein are well documented in the prior art. For example, thiols of the formula $R_fR'$—SH have been described in a number of U.S. Patents including U.S. Pat. Nos. 2,894,991; 2,961,470; 2,965,677; 3,088,849; 3,172,190; 3,544,663 and 3,655,732.

Thus, U.S. Pat. No. 3,655,732 discloses mercaptans of formula $$R_f-R'-SH$$

where R' is alkylene of 1 to 16 carbon atoms and $R_f$ is perfluoroalkyl and teaches that halides of formula $R_f$—R'—hal are well-known; reaction of $R_fI$ with ethylene under free-radical conditions gives $R_f(CH_2CH_2)_aI$ while reaction of $R_fCH_2I$ with ethylene gives $R_fCH_2(CH_2CH_2)_aI$ as is further taught in U.S. Pat. Nos. 3,088,849; 3,145,222; 2,965,659 and 2,972,638.

U.S. Pat. No. 3,544,663 teaches that the mercaptan $$R_fCH_2CH_2SH$$

where $R_f$ is perfluoroalkyl of 5 to 13 carbon atoms, can be prepared by reacting the perfluoroalkyl alkylene iodide with thiourea or by adding H$_2$S to a perfluoroalkyl substituted ethylene ($R_f$—CH=CH$_2$), which in turn can be prepared by dehydrohalogenation of the halide $R_f$—CH$_2$CH$_2$—hal.

The reaction of the iodide $R_f$—R'—I with thiourea followed by hydrolysis to obtain the mercaptan $R_f$—R'—SH is the preferred synthetic route. The reaction is applicable to both linear and branched chain iodides. Many useful perfluoroalkoxyalkyl iodides are described in U.S. Pat. No. 3,514,487 of general formula $$(CF_3)_2CFOCF_2CF_2(CH_2CH_2)_mI$$

where m is 1–3.

Particularly preferred herein are the thiols of formula $$R_fCH_2CH_2SH$$

where $R_f$ is perfluoroalkyl of 6 to 12 carbon atoms. These $R_f$-thiols can be prepared from $R_fCH_2CH_2I$ and thiourea in very high yield.

Compounds of this invention which are preferred are those where $R_f$ is perfluoroalkyl of 6 to 12 carbon atoms or said perfluoroalkyl substituted by perfluoroalkoxy of 2 to 6 carbons atoms, $R_1$ is branched or straight chain alkylene of 2 to 8 carbon atoms, alkylenethioalkylene of 2 to 8 carbon atoms, alkylenoxyalkylene of 2 to 8 carbon atoms or alkyleneiminoalkylene of 2 to 8 carbon atoms where the nitrogen atom contains hydrogen or methyl as a third substituent;

$R_2$ is hydrogen, straight chain alkyl of 1 to 4 carbons, phenyl, or —B—COOH;

g is 1, and B is a covalent bond or is an alkylene bridging group with 1 to 6 carbon atoms.

Particularly preferred are those compounds where $R_f$ is perfluoroalkyl of 6 to 12 carbon atoms, $R_1$ is alkylene of 2 to 4 carbon atoms, $R_2$ is hydrogen or alkyl of 1 or 2 carbons, g is 1, and B is a covalent bond or an alkylene bridging group with 1 to 3 carbon atoms.

One group of preferred compounds has the formula $$(R_fCH_2CH_2S)_2C(CH_3)-CH_2CH_2COOH$$

where $R_f$ is perfluoroalkyl of 6 to 12 carbon atoms or where $R_f$ is perfluoroalkoxyperfluoroalkyl or 5 to 15 carbon atoms, and especially where $R_f$ is $(CF_3)_2CFO(CF_2CF_2)_y$— and y is 1 to 6.

Another group of preferred compounds have the formula $(R_fCH_2CH_2S)_2C(CH_3)COOH$ where $R_f$ is perfluoroalkoxyperfluoroalkyl of 4 to 12 carbon atoms, and especially where $R_f$ is $(CF_3)_2CFO(CF_2CF_2)_y$— where y is an integer from 1 to 6.

In many cases the corresponding α or β-keto esters are more suitable for reaction since they are generally available or have better stabilities. The following aldehydo acids, keto acids, aldehydo esters and keto esters are listed for illustrative purposes.

| ALDEHYDO AND KETO ACIDS OR ESTERS THEREOF | |
|---|---|
| glyoxylic acid | O=CHCOOH |
| pyruvic acid | $CH_3COCOOH$ |
| 2-ketobutyric acid | $CH_3CH_2COCOOH$ |
| ketomalonic acid | $O=C(COOH)_2$ |
| 2-ketoglutaric acid | $O=CCH_2CH_2COOH$ |
| oxalpropionic acid | $\underset{\underset{COOH}{\mid}}{CH(CH_3)COOH} \overset{O}{\overset{\parallel}{}}$ |
| acetoacetic acid | $CH_3COCH_2COOH$ |
| 2-methylacetoacetic acid | $CH_3COCH(CH_3)CO_2H$ |
| oxalacetic acid | $\underset{\underset{CH_2COOH}{\mid}}{O=C-COOH}$ |
| benzoylacetic acid | $\phi COCH_2COOH$ |
| acetylsuccinic acid | $\underset{\underset{CH_2COOH}{\mid}}{CH_3COCH_2COOH}$ |
| 2-acetylglutaric acid | $\underset{\underset{CH_2CH_2COOH}{\mid}}{CH_3COCHCOOH}$ |
| levulinic acid | $CH_3COCH_2CH_2COOH$ |
| 4-ketopimelic acid | $O=C(CH_2CH_2COOH)_2$ |
| 3-benzoylpropionic acid | $\phi COCH_2CH_2COOH$ |
| 4-benzoylbutyric acid | $\phi COCH_2CH_2CH_2COOH$ |
| 5-benzoylvaleric acid | $\phi COCH_2CH_2CH_2CH_2COOH$ |
| 5-ketohexanoic acid | $CH_3\overset{O}{\overset{\parallel}{C}}CH_2CH_2CH_2COOH$ |

The novel gem-perfluoroalkylthio $R_f$-acids be convertered into esters and anhydrides employing standard synthetic techniques as illustrated below:

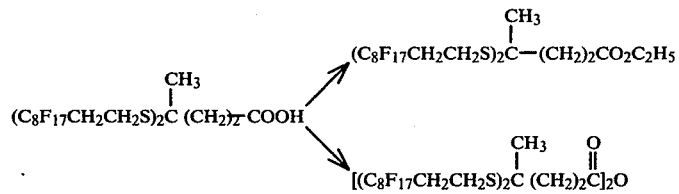

Chrome complexes which may be made in accordance with established procedures are useful for rendering paper, leather and textiles oil repellent.

In the case of $R_f$-esters, it is frequently preferable to first make the acid derivative since the acidic reaction conditions necessary for mercaptal or mercaptol formation might favor hydrolysis of the preformed ester function.

All novel $R_f$-acids, esters or anhydrides described herein are characterized by having a pair of closely packed $R_f$-groups in each molecule. This is the most important fact since polycondensation products derived from these novel $R_f$-acids will show, due to the close packing of the $R_f$-groups, significantly higher oil repellency ratings than condensation products derived from diacids containing just one $R_f$-group.

Although aldehydo or keto functions are generally most suitable, displacement with the mercaptan will also occur on acetals or ketals by the use of boron trifluoride etherate. Displacement of active methylene groups, such as in malonic and acetoacetic esters is also reported and products can be formed thusly, but the generally recommended method is through an aldehydo or keto function.

The formation of mercaptal is generally believed to go in two stages:

$$RCHO + HSR^1 \rightleftharpoons RCH(OH)SR^1$$

$$RCH(OH)SR^1 + HSR^1 \rightleftharpoons RCH(SR^1)_2 + H_2O$$

The first reaction frequently takes place on mixing the reactants. The second requires an acid catalyst; mercaptoles are formed similarly. Zinc chloride is sometimes required to push the reaction although it is usually spontaneous.

With less reactive carbonyls the reaction may take hours or days. with ketonic functions hindered by branched alkyl or phenyl groups near the carbonyl, the reaction is sluggish. Methyl ketones, e.g., MeCO . . . COOH, are particularly reactive.

Diketones having carbonyls, separated by at least one carbon atom, behave independently and thus compounds having a higher multiplicity of $R_f$-groups might be made.

The preparation of mercaptal or mercaptole is usually carried out in a solvent in which the reactants are soluble and the product is not at the reaction temperature employed. Suitable solvents are aliphatic or aromatic hydrocarbons such as heptane, benzene, toluene, etc.; chlorinated or fluorinated aliphatic or aromatic hydrocarbons such as methylene chloride, chloroform, methyl chloroform, carbon tetrachloride, trichloroethylene, perchloroethylene, Freons' such as 1,1,2-trifluoro-1,2,2-trichloroethane, etc., chlorobenzene, benzotrifluoride or hexafluoroxylene, esters and ethers such as ethyl acetate and higher homologs, dialkyl ethers, tetrahydrofuran, ethylene glycol monomethyl or monoethyl ether, ethylene glycol dimethyl or diethyl ether, and mixtures of these esters or esters with water.

The addition reaction is very simple to carry out, i.e., the $R_f$-mercaptan, and keto (or aldehydo) acid are dissolved at the desired molar ratios in a solvent described above or reacted neat and the catalyst is bubbled in slowly.

The reaction mixture is kept at a temperature ranging from room temperature to 80° C., under nitrogen, until gas chromatography of the reaction mixture indicated that the free mercaptan is essentially consumed. Visual observation of product precipitation or titration of free mercapto groups or TLC (thin layer chromatography) are other means of following the reaction.

Required reaction times depend on reaction temperatures, amounts, compound reactivities, and on the catalyst employed and may range from 5 minutes to 1 week. The products can be isolated by filtration or by evaporation of solvent and catalyst, and can be purified employing crystallization, precipitation or distillation. The preferred catalyst recommended for formation of the subject acids is anhydrous hydrogen chloride, although concentrated hydrochloric acid, boron trifluoride, zinc chloride, and other Lewis acids may be used.

The oxidation of the subject $R_f$-mercaptals or $R_f$-mercaptoles to gem-sulfoxides or more generally the sulfones is most usually accomplished with potassium permanganate, although chromate, nitric acid, persulfate and hydrogen peroxide are suitable.

Such fluorochemical surfactants are useful to improve or impart properties such as: wetting, penetration, spreading, leveling, foam stability, flow properties, emulsification, dispersion, and oil and water repellency. Based on these unique properties are numerous applications, some of which follow. Although applications are suggested for a particular use area, the general applicability of each concept is inferred for other applications.

PLASTICS AND RUBBER INDUSTRY

Emulsifying agent for polymerization, particularly fluoromonomers
　As a latex stabilizer
　To aid in the preparation of agglomerates of powdered fluorocarbon polymers
　In synergistic mixtures with hydrocarbon surfactants to wet low energy surfaces including natural and synthetic rubbers, resins, and plastics
As an adjuvant for applications and as foaming agents to aid in leak detection
As a foam additive to control spreading, crawling, edge build up
　As mould release agents, for silicones, etc.
In refractory processes
As an anti-mist film former
Additive for elimination of trapped air in plastic laminates
Wetting agent for resin molds for definition, strength
Hot-melt additive for oil and grease repellency
Resin additive for improved wetting of and bonding with fillers
Flow modifier for extruding hot melts: spreading, uniformity, anti-cratering
Adjuvant for resin etchant
Mold release agent, demoulding agent
Retarder for plasticizer migration or evaporation
Internal antistatic agent for polyolefins
Antiblocking agent for polyolefins

PETROLEUM INDUSTRY

Wetting assistant for oil well treatments, drilling muds
As a film evaporation inhibitor for gasoline, jet fuel, solvents, hydrocarbons
Lubricating, cutting oil improver, to improve penetration times
In extreme pressure EP lubricants
Oil spill collecting agent
Additive to improve tertiary oil well recovery

TEXTILE AND LEATHER INDUSTRIES

Soil release and soil proofing agent
Oil/water repellent textile and leather treatment
Wetting agent to improve coverage and penetration of pores of substrates
Anti-foaming agent in textile treatment baths
Wetting agent for finish-on-yarn uniformity
Penetrating agent for finishes on tow, heavy denier fibers
Emulsifying agent/lubricant/for fiber finishes
Cleaner/metal treating agent for polymerization equipment
Flow modifier for spinning of hot melts, solutions
Additive for fabric finishes for spreading, uniformity
Wetting agent for dyeing
Penetration aid for bleaches
Wetting agent for binder in nonwoven fabrics

PAINT, PIGMENT AND FINISHING INDUSTRIES

Leveling, anti-cratering adjuvant for finishes and paints
Adjuvant for control of soiling
Agent to control differential evaporation of solvents
Leveling agent for floor waxes
Adjuvant for waxes to improve oil and water repellency
Adhesion improver for oily or greasy surfaces
To combat pigment flotation problems
Improver for automative finishes, based on water-based coatings in which the pigments are rendered nonreactive
Pigment grinding aid to promote wetting, dispersion, color development
Foam generator substance for the application of dyes, inks
Electrolytic conversion coatings

MINING AND METALWORKING INDUSTRIES

In cleaning agents for property improvement
Additive for solvent cleaning
Additive for metal pickling baths to increase both life and acid runoff
Additive for chrome electroplating: surfact tension reduction, foaming
Additive for soldering flux, especially for electronic circuitry
Protective agent for coatings (tarnish resistance, grease repellency)
Corrosion inhibitor
Additive for etchant solution for improved definition
To form antimist films and anti-condensation surfaces
Plastic preplate and silicon etchant technology
In soldering flux for microelectronics to reduce foaming
In chemical roughing agent solutions, prior to galvanization
As a colloidal dispersion aid for magnetic solids
Protective coatings for aluminum and as an antiblocking agent
Wetting agent for leaching copper ores and as a froth flotation agent
To promote ore wetting and quicker breaking of the protective oxide layer

PHARMACUETICAL INDUSTRY

Improve the properties and penetration of antimicrobial agents
Improve the properties of biochemicals, biocides, algicides, bacteriocides, and bacteriostats
Improve the strength, homogeneity, and reduce the permeability of encapsulated materials
Emulsify fluorochemical blood substitutes

AGRICULTURE AND FORESTRY

Wetting agent for herbicides, flungicides, weed killers, hormone growth regulators, parasiticides, insecticides, germicides, bactercides, nematocides, microbiocides, defolients and fertilizers
As an ingredient in chemosterilents, insect repellents and toxicants
For wettable powder pesticides and chemical powders
Corrosion inhibitor for chemical applicators
Wetting agent for foliage
Wetting additive for live stock dips, or to wet sheep skins during desalination Wetting adjuvant for manufacture of plywood veneer
Penetrant for preservative impregnation
Pulping aid
For cleaning tubes in paper making, dyeing
Grease/oil repellents for paper

FIRE FIGHTING

Wetting agent for fighting forest fires
Ingredient of AFFF, aqueous film forming extinguishing agents
Component of fluoroprotein foams
Additives to dry chemical extinguishing agents
Agent in aerosol-type extinguishers
Wetting agent for springler water

AUTOMOTIVE, BUILDING MAINTENANCE AND CLEANING

Wetting agent for cleaning compositions
Additive for alkaline cleaners
Glass cleaner
Wetting agent for automobile waxes
Adjuvant to improve oil/water repellency of wax
Lubricant/corrosion inhibitor for antifreeze
Rinse-aid for car washes
In dry cleaning compositions and solvent cleaners, for water displacement and foaming. May improve soil suspension and decrease redeposition
Foaming agents for pipe cleaning
Anti-mist film foamer for glass and plastics
In foams for dust suppression
Cleaner for building exteriors
For acidic concrete cleaners
Air entrainment additive for low density concrete
Bubble foamer for air tracing, in ventilating systems

HOUSEHOLD, COSMETIC AND PERSONAL PRODUCTS

Rinse-aid for dishwashing
Liquid polishing compositions
Floor polish leveling agent
Additive for alkaline oven cleaners
Synergistic improver for disinfectants
Carpet cleaners
Synergistic wetting agent in detergent formulations
Additive for protective coatings on metals (tarnish resistance, grease resistance)
Gloss and antistatic improver
Hair shampoo ingredient
Shaving foam ingredient
Oil and water repellent cosmetic powders ingredient
Ingredient of lotions of creams for skin or hair
Ingredient of skin protection creams

PHOTOGRAPHY AND GRAPHIC ARTS

Printing ink additive for ink flow and leveling, both aqueous and solvent based
Wetting agent for writing inks
To combat pigment flooding and flotation in printing inks
To form ink repellent surfaces for waterless lithoplates, or electrographic coatings
Prevent reticulation of gelatin layers and improve uniformity
Assist in film drying
Improve film coatings and reduce "contraction flecks"

Wetting, leveling, anti-cratering assit agent
Surfactant for developer solutions Photoemulsion stabilizer
Prevent photo-lubricant agglomeration
Coating aid in the preparation of multiple layer film elements
Antistatic wetting agent for film coatings
Antifogging agent for films
Bonding agent for fillers and fluoropolymer films
In coatings for nematic liquid crystal cells

EXAMPLE 1

4,4-Bis(1,1,2,2-tetrahydroperfluorodecylthio)pentanoic acid $(C_8F_{17}CH_2CH_2S)_2C(CH_3)CH_2CH_2COOH$ 1,1,2,2-tetrahydroperfluorodecanethiol (28.8 gm, 0.06 mole), 4-ketopentanoic acid (4.64 gm, 0.04 mole), and glacial acetic acid (47.7 gms) were added to a 150 ml one neck r.b. flask with a magnetic stirring bar. Anhydrous hydrogen chloride was bubbled through the solution for 10 minutes with stirring. Within 7 minutes a white precipitate began to form and the mixture partially solidified. Another 40 gms of glacial acetic acid were added, the mass was broken up, and the stirring was continued for 1 hour. The mixture was filtered through a fritted disc funnel (24–50μ) and washed with 2000 ml glacial acetic acid. The product was dried (19.8 gms). The mother and wash liquors were combined, stripped of acetic acid, to a 50 ml volume, retreated with HCl, filtered, washed, and dried (4.75 gms). The above process was repeated a third time (1.7 gms). The total product (26.05 gms, 82.8% yield) was crystallized twice from carbon tetrachloride to yield 26.05 gms of product (m.p. 105.8°–106.4° C.). A TLC check showed the product free of starting material. Resistance to basic hydrolysis was proven by refluxing 0.66 gms of the subject acid in 22 gms 1.0 N alcoholic potassium hydroxide for four hours. Neutralization and work-up led to the recovery of 0.56 gms (85% recovery).

TGA scan in both air and nitrogen was identical. The data showed constant weight to about 155° C., and then weight loss at an increasing rate to completion by 260°–265° C. The weight loss (both atmospheres) is characteristic of vaporization as opposed to decomposition.

Analysis for $C_{25}H_{16}F_{34}O_2S_2$: Calc.: C, 23.37; H, 1.52; F, 61.03. Found: C, 28.34; H, 1.62; F, 61.26.

EXAMPLE 2

4,4-Bis(1,1,2,2-tetrahydroperfluorooctylthio)pentanoic acid $(C_6F_{13}CH_2CH_2S)_2C(CH_3)CH_2CH_2COOH$ 1,1,2,2-Tetrahydroperfluorooctanethiol (7.6 gms, 0.02 mole) and 4-ketopentanoic acid (1.16 gms, 0.010 moles) were added to a 25 ml Erlenmeyer flask equipped with a magnetic stirring bar. Anhydrous hydrogen chloride was bubbled through the reaction for 20 minutes until a white precipitate formed. After standing 10 minutes, the reaction was quenched with water, precipitated from hexane, crystallized from carbon tetrachloride, filtered, and dried (3.4 gms, 39% yield, m.p. 74'–75° C.). An I.R. scan showed the disappearance of

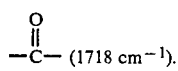
(1718 cm$^{-1}$).

Analysis for $C_{21}H_{16}F_{26}O_2S_2{}^2$:
Calc.: C, 29.31; H, 2.11; F, 57.41. Found: C, 29.18; H, 1.79; F, 56.31.

EXAMPLE 3

4,4-Bis(1,1,2,2-tetrahydroperfluoroalkylthio)pentanoic acid $(R_fCH_2CH_2S)C(CH_2CH_2COOH)$ 1,1,2,2-Tetrahydroperfluoroalkanethiols (48.0 gms, 0.1 moles), 4-ketopentanoic acid (8.15 gms, 0.07 moles), and glacial acetic acid (83.85 gms) were added to a 250 ml, 1 neck, r.b. flask equipped with a magnetic stirring bar. Anhydrous hydrogen chloride was bubbled through the stirred solution for 0.5 hour. A white precipitate formed and after another hour and reaction was quenched with water, filtered, washed with hexane, and dried (45.9 gms, 85.3% yield, m.p. 82.5°–94° C.). 1.585 gms was dissolved in methanol and titrated potentiometrically with 14.5 ml 0.1 N alcoholic potassium hydroxide. Equivalent weight—1091 (found), 1064 (calculated). (perfluoroalkyl represents a mixture of 23% C6, 49% C8 and 25% C10).

EXAMPLE 4

2,2-Bis(1,1,2,2-tetrahydroperfluorodecylthio)propanoic acid $(C_8F_{17}CH_2CH_2S)_2C(CH_3)COOH$ 1,1,2,2-Tetrahydroperfluorodecanethiol (4.8 gms, 0.01 mole), 2-ketopropanoic acid (0.44 gms, 0.055 mole), and glacial acetic acid (6.99 gms) were added to a 25 ml Erlenmeyer flash containing magnetic stirring bar. Anhydrous hydrogen chloride was bubbled through the solution for 1 hour and the reaction was then stirred overnight. The white precipitate which formed was washed with water, filtered, dried, precipitated from hexane, then crystallized from carbon tetrachloride, and dried (3.2 gms, 62.1 yield, m.p. 86.8°–88.2°). A TLC check showed one component.

Analysis for $C_{23}H_{12}F_{34}O_2S_2$: Calc.: C, 26.81; H, 1.17; F, 62.69. Found: C, 27.05; H, 1.17; F, 62.57.

EXAMPLE 5

4,4-Bis(1,1,2,2-tetrahydroperfluorooctylthio)heptanedioic acid $(C_6F_{13}CH_2CH_2S)_2C(CH_2CH_2COOH)_2$ 1,1,2,2-Tetrahydroperfluorooctanethiols (5 gms, 0.013 mole), 4-ketoheptanedioc acid (0.9 gm, 0.0052 mole), and glacial acetic acid (13.8 gms) were placed in a 25 ml Erlenmeyer flask containing a magnetic stirring bar. Anhydrous hydrogen chloride was bubbled through the mixture for 1 hour and the reaction was then stirred overnight. A white ppt was filtered from the reaction mixture, washed with water followed by hexane, precipitated from a mixture of acetone and hexane (20/80) and dried. (m.p. 134°–134.5°.)

Analysis for $C_{23}H_{18}F_{26}O_4S_2$: Calc.: C, 30.14; H, 1.98; F, 53.89. Found: C, 30.11; H, 1.88; F, 54.23.

Using the methods described and by techniques similar to Examples 1–5, the following additional perfluoroalkyl carboxylic acids are prepared:

Examples 6–20

| Thiol | Aldehydo or Keto Acid | Product |
|---|---|---|
| 6. $(CF_3)_2CFOCF_2CH_2CH_2CH_2SH$ | $CH_3CH_2COCOOH$ | $[(CF_3)_2CFOCF_2CF_2CH_2CH_2S]_2C(CH_2CH_3)COOH$ |
| 7. $(CF_3)_2CFOCF_2CH_2CH_2CH_2SH$ | $O=C(COOH)_2$ | $[(CF_3)_2CFOCF_2CF_2CH_2CH_2S]_2C(COOH)_2$ |
| 8. $(CF_3)_2CFOCF_2CH_2CH_2CH_2SH$ | $CH_3COCH_2COOH$ | $[(CF_3)_2CFOCF_2CF_2CH_2CH_2S]_2C(CH_3)CH_2COOH$ |
| 9. $C_6F_{13}CH_2CH_2SH$ | $\phi COCH_2COOH$ | $(C_6F_{13}CH_2CH_2S)_2C(\phi)CH_2COOH$ |
| 10. $C_6F_{13}CH_2CH_2SH$ | $O=C(COOH)CH_2COOH$ | $(C_6F_{13}CH_2CH_2S)_2C(COOH)CH_2COOH$ |
| 11. $CF_3CF_2CH_2SH$ | $O=C(CH_3)CH_2CH_2COOH$ | $(CF_3CF_2CH_2S)_2C(CH_3)CH_2CH_2COOH$ |
| 12. $CF_3CF_2CH_2SH$ | $CH_3COCH_2COOH$ | $(CF_3CF_2CH_2S)_2C(CH_3)CH_2COOH$ |
| 13. $C_8F_{17}(CH_2)_4SH$ | $O=C(COOH)_2$ | $(C_8F_{17}(CH_2)_4S)_2C(COOH)_2$ |
| 14. $C_8F_{17}CH_2CH_2OCH_2CH_2CH_2SH$ | $CH_3COCH_2COOH$ | $(C_8F_{17}CH_2CH_2OCH_2CH_2CH_2S)_2C(CH_3)CH_2COOH$ |
| 15. $C_8F_{17}CH_2CH_2N(CH_3)CH_2CH_2CH_2SH$ | $CH_3COCH_2COOH$ | $[C_8F_{17}CH_2CH_2N(CH_3)CH_2CH_2CH_2S]_2C(CH_3)CH_2COOH$ |

Examples 21–25
Oxidation Products of Aldehydo and Keto Acid Derivatives

| | |
|---|---|
| 21. From Example 8 | $[(CF_3)_2CFOCF_2CF_2CH_2CH_2SO_2]_2C(CH_3)CH_2COOH$ |
| 22. From Example 1 | $(C_8F_{17}CH_2CH_2SO_2)_2C(CH_3)CH_2CH_2COOH$ |
| 23. From Example 4 | $(C_8F_{17}CH_2CH_2SO_2)_2C(CH_3)COOH$ |
| 24. From Example 14 | $(C_8F_{17}CH_2CH_2OCH_2CH_2SO_2)_2C(CH_3)CH_2COOH$ |
| 25. From Example 15 | $[C_8F_{17}CH_2CH_2N(CH_3)CH_2CH_2CH_2SO_2]_2C(CH_3)CH_2COOH$ |

EXAMPLE 26

Compounds of Examples 1–3 were dissolved in methyl isobutyl ketone and applied to polyester-cotton twill (65/35) in such a concentration that 0.20% fluorine was deposited onto the fabric. After the padding process, the fabrics were dried and cured at 250° F. for ten minutes.

The AATCC Oil Rating was determined according to Standard Test Method 118–1966T of the American Association of Textile Chemists and Colorists. Ratings are given from 0 (minimum) to 8 (maximum). A commonly accepted level on soil repellent fabrics in the U.S. is an oil repellency of 4.

| Compound of Example | Initial Oil Repellency |
|---|---|
| 1 | 4 |
| 2 | 5 |
| 3 | 4 |

What we claim is:
1. A perfluoroalkyl acid for the formula

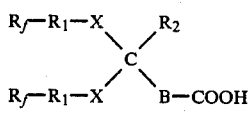

wherein $R_f$ is perfluoroalkyl of 1 to 18 carbon atoms, or said perfluoroalkyl substituted by perfluoroalkoxy of 2 to 6 carbon atoms;

$R_1$ is branched or straight chain alkylene of 1 to 12 carbon atoms, alkylenethioalkylene of 2 to 12 carbon atoms, alkyleneoxyalkylene of 2 to 12 carbon atoms, or alkyleneiminoalkylene of 2 to 12 carbon atoms where the nitrogen atom contains as a third substituent, hydrogen or alkyl of 1 to 6 carbon atoms;

X is —S—, —SO— or —SO$_2$—;

R$_2$ is hydrogen, straight or branched alkyl of 1 to 6 carbon atoms, phenyl, alkyl substituted phenyl of up to 18 carbon atoms or —B—COOH; and B is a covalent bond or alkylene of up to 18 carbon atoms.

2. A compound of claim 1 wherein

R$_f$ is perfluoroalkyl of 6 to 12 carbon atoms or said perfluoroalkyl substituted by a perfluoroalkoxy.

R$_1$ is branched or straight chain alkylene of 2 to 8 carbon atoms, alkylenethioalkylene of 2 to 8 carbon atoms, alkylenoxyalkylene of 2 to 8 carbon atoms or alkyleneiminoalkylene of 2 to 8 carbon atoms where the nitrogen atom contains hydrogen or methyl as a third substituent;

B is a covalent bond or an alkylene bridging group with 1 to 18 carbon atoms.

3. A compound of claim 1 wherein

R$_f$ is perfluoroalkyl of 6 to 12 carbon atoms,

R$_1$ is alkylene of 2 to 4 carbon atoms,

R$_2$ is hydrogen or lower alkyl and

B is a covalent bond or alkylene of 1 to 3 carbon atoms.

4. A compound of claim 3 having the formula (R$_f$CH$_2$CH$_2$S)$_2$C(CH$_3$)—CH$_2$CH$_2$COOH wherein R$_f$ is perfluoroalkyl of 6 to 12 carbon atoms or perfluoroalkoxyperfluoroalkyl of 5 to 15 carbons.

5. A compound of claim 4 wherein
R$_f$ is (CF$_3$)$_2$CFO(CF$_2$CF$_2$)$_y$— and y is 1 to 6.

6. A compound of claim 3 having the formula (R$_f$CH$_2$CH$_2$S)$_2$C(CH$_3$)COOH wherein R$_f$ is perfluoroalkoxyperfluoroalkyl of 4 to 12 carbons atoms or (CF$_3$)$_2$CFO(CF$_2$CF$_2$)$_y$—where
y is an integer from 1 to 6.

7. The compound of claim 1 which is 4,4-Bis(1,1,2,2-tetrahydroperfluoroctylthio)pentanoic acid.

8. The compound of claim 1 which is 4,4-Bis(1,1,2,2-tetrahydroperfluorodecylthio)pentanoic acid.

9. The Compound of claim 1 which is 4,4-Bis(1,1,2,2-tetrahydroperfluoroalkylthio)pentanoic acid.

10. The compound of claim 1 which is 2,2-Bis(1,1,2,2-tetrahydroperfluorodecylthio)propanoic acid.

11. The compound of claim 1 which is 4,4-Bis(1,1,2,2-tetrahydroperfluorooctylthio)heptanedioc acid.

* * * * *